United States Patent [19]

Nylander et al.

[11] Patent Number: 4,966,671
[45] Date of Patent: Oct. 30, 1990

[54] METHOD AND APPARATUS FOR ELECTROCHEMICAL ANALYSIS

[75] Inventors: Claes I. Nylander, Linköping, Sweden; Ian W. Burns, Kimbolton, England

[73] Assignee: Unilever Patent Holdings, Rotterdam, Netherlands

[21] Appl. No.: 208,806

[22] Filed: Jun. 20, 1988

Related U.S. Application Data

[63] Continuation of Ser. No. 106,955, Oct. 31, 1987, abandoned, which is a continuation of Ser. No. 925,557, Oct. 31, 1986, abandoned.

[30] Foreign Application Priority Data

Oct. 31, 1985 [GB] United Kingdom ............... 8526902

[51] Int. Cl.$^5$ ............................................. G01N 27/46
[52] U.S. Cl. ............................ 204/153.14; 204/415; 204/418; 204/153.15
[58] Field of Search ............... 204/1 T, 400, 1 A, 403, 204/415, 416, 417, 418, 1 N

[56] References Cited

U.S. PATENT DOCUMENTS

| | | | |
|---|---|---|---|
| 3,480,520 | 11/1969 | Smith | 204/400 |
| 3,865,708 | 2/1975 | Light | 204/1 N |
| 4,454,007 | 6/1984 | Pace | 204/416 |
| 4,668,346 | 5/1987 | Entwistle | 204/1 T |

OTHER PUBLICATIONS

Durst, "Ion Selective Electrodes", National Bureau of Standards Special Publication 314, (1969), pp. 359–373.

Primary Examiner—John F. Niebling
Assistant Examiner—Ben C. Hsing

[57] ABSTRACT

A potentiometric electrochemical analysis method, which comprises placing by capillary action an aqueous sample liquid to be tested for the presence of a quantity of an analyte in the sample liquid, in each of two compartments of an electrochemical analysis cell, wherein the aqueous sample liquid so placed in each compartment is in electrochemical contact with one of two electrodes forming part of the cell, wherein the electrodes are insensitive to the analyte, and wherein the compartments are separated by an electroactive barrier which is sensitive to or selective for the analyte, the barrier not being in electrical contact with either electrode except through the medium of the sample liquid, the method further comprising changing the amount of the analyte material in a selected one of the compartments by adding thereto a predefined standard quantity of analyte, measuring the resulting cell potential and determining the concentration of the analyte in the sample liquid, the predefined standard quantity of analyte being allowed to dissolve in the sample liquid from a dry material predosed in one of the compartments, the dry material being free from any electroactive material to which the electrode are sensitive.

2 Claims, 1 Drawing Sheet

METHOD AND APPARATUS FOR ELECTROCHEMICAL ANALYSIS

This is a continuation of application Ser. No. 106,955, filed Oct. 31, 1987, now abandoned, which is a continuation of Ser. No. 925,557, filed Oct. 31, 1986, now abandoned.

This invention relates to methods and apparatus for use in electrochemical analysis procedures.

PRIOR ART

The prior art includes potentiometric measurement methods in which a sample liquid is placed in contact with a reference electrode and another electrode with selectivity for a material to be analysed, and two potential measurements are made, one before and one after the addition to this system of a standardised concentration of the material for which the electrode is sensitive.

Also included in the prior art are a number of enzyme electrode measurement methods, in one of which an enzyme (urease) is chemically bound to a ptfe membrane which is an integral part of an ammonia gas membrane electrode incorporating an ammonia permeable membrane, (cf. M Mascini and C G Guilbault, Anal Chem. 49 (6) 1977, pp 795-798).

Also known are electrochemical cells mounted within capillary-fill devices, as described in European Patent Application No. 0 170 135 (Unilever).

SUMMARY OF THE INVENTION

It is an aim of this invention to provide new potentiometric electrochemical analysis methods and apparatus which are simple and convenient to use and also to provide methods which can be performed without calibration of the electrode system.

DETAILED DESCRIPTION OF THE INVENTION

Figure 1:
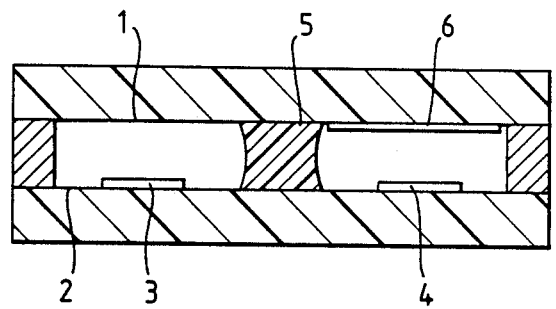
FIG. 1 is a diagrammatic cross-sectional scheme of an electrode-containing capillary cell device according to an embodiment of the invention.

According to the present invention we provide a potentiometric method of electrochemical analysis which comprises placing an aqueous sample liquid in each of two compartments of an electrochemical analysis cell, the liquid in each compartment being in electrochemical contact with one of the two electrodes (usually for example similar electrodes) forming part of the cell, the electrodes being insensitive to the material which is to be analysed in the sample, and the compartments being separated by an electroactive barrier which is sensitive or selective for the material which is to be analysed, and which is not in contact with either electrode except through the medium of the sample liquid, the method also comprising changing the amount of material to be analysed in one of the compartments by a standing quantity, e.g. by adding said standard quantity or releasing it or causing it to be released, in a form to which the electrodes are not sensitive, or by subtracting it or causing it to be subtracted, and measuring the cell potential to give an indication related to the concentration of the material to be analysed in the sample.

Suitable samples of materials to be analysed are ions such as potassium, sodium, or ammonium ions. The membrane separating the two halves of the cell needs to be an electroactive membrane of corresponding selective specificity, and can be for example based on a thin film of plasticised polyvinylchloride containing the corresponding ionophore.

Suitable electrodes are for example silver/silver halide, e.g. chloride or bromide electrodes, and these have the particular advantage that they can be reproducibly fabricated so that in principle the electrochemical cells made with them would show close to zero offset voltage in the absence of the additional standard quantity of the material to be analysed on one side of the membrane, and that by the use of for example the electrode constructions described below, this can be realised in practice.

The membrane material to be used in the practice of the present invention can be for example a polymer such as pvc, especially with a content of plasticiser. Suitable contents for the ionophore or other sensitising component are for example within the range 1-5% by weight of the whole membrane composition. The ionophore-containing membrane can be for example 0.1-1mm thick. The pvc that incorporates the ionophore or other sensitising component should usually incorporate conventional relatively large amounts of plasticiser, as used in known ionophor-pvc membranes, e.g. as a pvc:plasticiser composition in proportions for example in the range 1:1 to 1:2 by weight. Examples of plasticisers useful in connection with ion-selective polymer membranes, especially pvc membranes, include dioctyl phenyl phosphonate, diethyl adipate, dioctyl sebacate, trioctyl phosphate, and o-nitrophenyl phenyl ether. Examples of useful ionophores include calcium diisoctyl phenyl phosphate (for calcium-sensitive electrodes), valinomycin (for potassium-sensitive electrodes), tridodecylamine (for hydrogen-ion-sensitive electrodes), particles of silver chloride, bromide, or iodide (for corresponding halide-sensitive electrodes), particles of silver sulphide (for sulphide-sensitive electrodes), mixtures of particles of silver and copper sulphides (for electrodes sensitive to copper as well as to sulphide), and more generally a finely divided particulate form of any of the materials previously used in crystalline form for making single-crystal electrodes, can be incorporated into the polymer or other non-conducting matrix of the membrane, in sufficient amount to put the particles in electrically effective contact to enable to membrane to respond to the presence of the corresponding constituent of the surrounding solution to be tested or measured.

The additional material, in the case of the ionic analytes, can suitably be a salt of the same ion as the analyte, with a counterion which is inert in the cell measurement process. For example, in the case of a cell to measure potassium concentration, a suitable salt for addition can be potassium sulphate or nitrate, or other soluble salt (but not chloride, where in the example under consideration the electrode is sensitive to chloride).

Alternatively, the addition can be caused by any other suitable process, e.g. an enzyme can be provided in one compartment to release an electro-analysable material from a substance present in the sample, (e.g. urease to release ammonium ion from urea); if desired a constant quantity of ammonium ion (in this example)

can be added to the other compartment or to both compartments.

Alternatively, subtraction of a standard quantity of material can be achieved for example by releasing a chelating agent, (preferably a strong complexing agent) for it, (e.g. EDTA), or an agent that precipitates it, or by any other suitable process. Most preferably the standard quantity subtracted, i.e. the standard quantity which the treatment is capable of subtracting, is appreciably less, and preferably also slightly less, than the lowest quantity initially expected in the samples to be examined.

In many cases, the best appropriate quantity of salt to be added to one side of the electroactive barrier in the practice of this invention can be judged by the expected range of concentration of the analyte in the liquids to be tested: it is preferred to choose as the standardised quantity of ion to be added, a sufficient amount to provide a concentration equal to the concentration at the middle of the expected sample range. For example, normal blood serum contains of the order of 5 mM potassium and 140 mM sodium, and these are suitable concentrations to provide as the standardised addition to one side of the respective measurement cells. Similar considerations apply to other materials for changing the analyte concentrations, e.g. enzymes and chelating agents.

Analysis kits provided according to the invention include dry components to form a compartmentalised electrochemical analysis cell of the type described above, in which two compartments, each containing an electrode, are separated by a membrane, (especially one that is spaced from, i.e. not in mechanical contact with, the electrodes) which is selective/sensitive to a material to be analysed and to which the electrodes themselves are not sensitive.

In preferred embodiments, one of the compartments contains, e.g. in the form of a coating on a surface, a standard quantity of the material for which the membrane is selective, or a reagent for generating or releasing such a material. In use, a defined volume of sample liquid is added to such a compartment so that the defined quantity of the material represents also a standard concentration.

Described below are examples of arrangements involving a two compartment device, in which the two compartments are separated by an ion selective membrane, and in which an electrode is located in each compartment.

In use, the sample liquid is introduced into both compartments, and an addition of appropriate salt is made into one compartment. The addition is a defined amount of a salt comprising a catron (or anion) to which the membrane is permeable and an anion (or cation) to which the membrane is impermeable. The choice of electrodes and addition material must be made so that the electrodes are not sensitive to any of the differentially added components. "Addition of a defined amount" means that the addition increases the concentration of the cation (or anion) to be analysed by a given (known, determinate or determinable) number of moles per litre of the additive.

The difference in concentration in the two compartments of the cation (or anion) to be analysed gives rise to a voltage between the two compartments. Because of the non-linear relation between concentration difference and voltage (ideally following Nernst's law) the voltage which can be measured between the two electrodes is a function of the initial concentration in the sample of the cation (or anion) to be analysed.

Another arrangement according to an embodiment of the present invention comprises a similar structure of compartments, electrodes and a membrane, but instead of a salt, an enzyme is added to one compartment. The enzyme converts a substrate into an ionic species to which the membrane is permeable.

The enzymatically produced concentration difference between the two compartments gives rise to a voltage between the two electrodes in the same way as in the version last described above.

In both versions (addition of salts or enzymes) the addition can be made before the electrical measurement, i.e., the salt or enzyme can be introduced in a dry or slightly hydrated form during manufacture of the device. The enzyme can also be immobilised on one or more surfaces inside one compartment, and does not necessarily have to be released into the sample liquid.

A convenient example form of cell for use in the practice of the invention comprises two substantially parallel opposed layers of glass or plastics, air-spaced by about 0.1 to 1 millimeter, which, together with an incomplete frame of bonding material located between them, (having at least one opening for the inward passage of liquid and possibly also the outward passage of air), form a capillary cell able to take up a defined volume of aqueous liquid. Mounted within the capillary cell is an electroactive membrane partition dividing the cell into two compartments so that the liquid contents are out of contact with each other except through the membrane. One of the glass or plastics layers can extend beyond the opening of the cell to enable a drop of liquid to be placed on its surface and pass either wholly or partly into the cell. Especially in versions of devices which are made of plastics material, an aperture can be made or left in one of the walls of the cell to allow sample loading, preferably with a filter device occupying the opening: at least one effective aperture is present for each compartment.

It can be useful to take steps to promote the capillary filling of the devices described herein, when plastic sheet material is used as the basis for the cells. One or both plates (e.g. the plate not carrying the electrodes, which can be the top plate), can be coated by spraying with for example a 10% w/v solution of polyvinylpyrrolidone (mw, 44,000) in ethanol, or a solution of Triton-X-100 (Trade Mark) surfactant, and allowing the solution to dry. This measure may for example be needless in the case of the gel-filled cells of Example 3 below.

Figure 2:
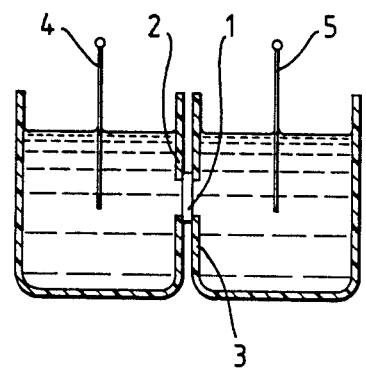
FIG. 2 is an electrochemical cell for potentionmetric analysis according to a second embodiment of the invention.

The invention is further explained by means of the following non-limitative Examples and accompanying drawings, FIGS. 1 and 2.

EXAMPLE 1

FIG. 1 of the accompanying drawings shows in diagrammatic cross-sectional scheme an example of an electrode-containing capillary cell device according to an embodiment of the invention. In FIG. 1, at numerals 1 and 2 there are shown opposite walls of the capillary cell. Other structure apart from electrodes and a partition, e.g., part of the circumferential sealing materials, handling pieces, and sample intake lip, and intake apertures, is omitted for clarity. The capillary gap can conveniently be of the order of 0.1-1 mm.

The capillary cell device is of a size to be handled easily, e.g. about 5cm×2.5cm. Alternative examples can be smaller, e.g. 2cm×1cm. The device comprises an upper (e.g. plastics, glass, or ceramic) plate and a lower (e.g. similar) plate (about 1mm thick) fixed together in parallel and spaced relation, less than 1mm apart, by bonding tracks of suitable (e.g. epoxy) adhesive to form a capillary cell cavity, open at one or both ends, which communicates with the outside through a first discontinuity in the bonding arranged to form a cell aperture at one side of the plates. Another discontinuity can be present at the other end of the bonding tracks, to leave another aperture, to allow exit of air when a sample liquid is loaded into the cell. One plate is larger than the other plate and has an end portion extending away from the aperture. This end portion acts as a platform or threshold or lip onto which a droplet sample liquid can be applied, so that this liquid can be made to fill the capillary cell cavities by capillary flow. The cavity attracts and contains a definite and adequately reproducible volume of liquid when loaded in this way.

Spaced-apart electrodes 3 and 4 are shown as layers fixed to the surface of wall 2 of the cell. Electrodes 3 and 4 are silver-silver halide electrodes, most preferably silver-silver chloride electrodes, made by applying and drying conductive paint onto the surface of wall 2, the conductive paint being a silver-particle-containing conductive paint as commercially available and used in the fabrication of hybrid electronic circuitry.

The electrodes so formed can be chloridised in per se conventional manner, (e.g. by dipping in potassium chlorochromate or by anodisation or other suitable method), to give surface-layer-form silver/silver chloride electrodes.

In the device of FIG. 1 a membrane barrier 5 less than 1 mm thick separates the two silver/silver chloride electrodes: this can be applied as a track of material comprising a mixture of pvc, solvent, plasticiser and ionophore (e.g., valinomycin in the case of a potassium-selective membrane) to one of the plates before the second plate is applied to form the capillary cell. The track of material can be applied for example by screen-printing, as can the other layers of materials to be deposited.

A suitable example composition for the track of material is 1% valinomycin, 66% dioctyl sebacate and 33% polyvinylchloride dissolved in tetrahydrofuran, e.g. at a concentration of about 0.08–0.1 gram of the mixture per ml of the solvent.

A releasable layer 6 containing potassium nitrate is coated on the wall of the capillary cell opposite one electrode. This coating is a releasable coating (e.g. a sucrose glaze) to be released into one compartment only and to dissolve in the sample liquid to give a standard concentration of potassium ion when this is taken up into the capillary cell.

In a preferred alternative, in place of sucrose, polyvinylpyrrolidone, (50% w/v) is used as a carrier base in which to dissolve the salt which is to form a releasable layer. Also, 2% cellulose acetate dissolved in cyclohexanone, is preferably sprayed lightly over the releasable coating to form when dry an additional thin surface layer which acts to retard the release of salt when the cell is filled. The salt/pvp layer dries quickly in atmospheric air after screen-printing, and the cellulose acetate is applied after it has dried.

EXAMPLE 2

Per se-conventional chloride-sensitive electrodes suitable for the practice of another embodiment of the present invention can be made and used by cleaning silver wire and subjecting it to the following treatment: the wire is given an ohmic contact at one end and chlorided by anodization, for example in 0.1M HCl solution opposite a platinum cathode at a current density of about 1 milliamp per $cm^2$ of silver electrode surface for about 250 seconds. The anodized electrode, now with a surface content of silver chloride, is rinsed and may be stored, for example, in purified (deionised) water preferably at least 24 hours before use.

In this embodiment of the invention, a plasticised polyvinylchloride membrane containing a potassium-selective ionophore is made by casting a mixture as used in Example 1 on to a smooth substrate and allowing the mixture to dry to a thickness of about 0.45 mm, and to give a membrane with a diameter of about 5 mm. Referring to FIG. 2, the membrane 1 so formed is clamped between two apertured plastics plates 2,3, each forming a wall of a liquid sample container in which an electrode 4,5 is located, so that the membrane forms the only electrochemical communication between the containers. Potassium concentrations can be measured easily by the use of the apparatus comprising the above-described compartments, membranes and electrodes, for example in aqueous liquids based on compositions approximately in the range NaCl 8 g/l, KCl 0.21 g/l, $KH_{2pl}\ PO_4$ 0.18 g/l, $CaCl_2.2H_2O$ 0.37 g/l, $MgSO_4.7H_2O$ 0.25 g/l, ("artificial plasma").

The standard addition is made as potassium nitrate in an amount sufficient to bring the K concentration on one side of the membrane to approximately 1.5–3.5 times the initial K concentration.

The potassium concentration in this medium before any addition is made is about 2.4 (on a negative log 10 molar scale) and it is found that concentrations of potassium up to 1.15 give an electrode output voltage range of about 70 millivolts.

EXAMPLE 3

A presently preferred example of materials to prepare an electrochemical analysis cell according to an embodiment of the invention is as follows:

A capillary-fill cell is made according to the general pattern of Example 1 and FIG. 1, with a preferred composition as follows to be used for the track of material to be screen-printed onto one of surfaces 1 or 2 to provide electroactive barrier 5:

(a) In the case of a potassium-sensitive cell a screen-printing composition is preferably made as follows:
Mix 44.5g dioctyl phthalate
5.5g pvc of m.w. 100,000,
12.5g cyclohexanone, together, and heat to dissolve the pvc, to give a solution. To this is added a solution containing :
0 5g valinomycin (in the case of a potassium-sensitive electrode) dissolved in 2.5 ml of tetrahydrofuran, (containing 5 mgm of potassium tetrakis-parachlorophenyl borate) at a temperature below 50° C., with stirring.

To the mixture is added:
12.5g of 5-micron ptfe particles (from BDH) (slowly while stirring vigorously).

This composition is used for screen-printing an ion-sensitive membrane.

(b) In the case of a sodium-sensitive cell, the composition is preferably varied as follows: Monensin (ionophore for making sodium-sensitive membranes) is used instead of valinomycin in a 1-gram amount, and with proportionately more THF to produce a solution which is then used in place of the valinomycin solution.

A pre-dosed dry quantity of potassium or sodium salt respectively is added to one only of the compartments of each respective cell as follows. The ion is inserted as a halide-free salt of potassium or sodium respectively, in a hydrophilic gel. The gel is formed in situ in one of the compartments. If desired a similar gel but lacking the ion is formed in the other compartment.

For the potassium-sensitive cell the gelling mixtures comprise:

2.9g acrylamide,
50 mg methylene-bis-acrylamide,
12.2g water, and (to a standardised final concentration) 0.58g $K_2CO_3$, made up together into a solution.

To these are added 0.6g of acrylic acid including 10mg photoinitiator ("Irgacure 184" (Trade Mark)).

Stir to clear any effervescence. Use this liquid to fill one compartment of the potassium-sensitive capillary-fill device. Fill the other compartment with a composition which is similar but omits the potassium salt and acrylic acid.

Expose to UV light until polymerisation is complete. Dry the resulting small aliquots of weak gel in the cell compartments under reduced pressure at room temperature.

This provides a standardised concentration of $K^+$ of the order of 5mM added on one side only of the membrane.

It is also found that the cells of the types described above show good internal consistency and relative freedom from long term divergence between the potentials of the electrodes of similar type, so that the voltage offsets generated while the devices are in storage before use can be very small.

Among the variations which can be made in the practice of the invention described above, we include the (preferred) use of small particles (e.g., about 20p silica gel particles by weight based on the weight of the whole composition, 15 microns in size as obtained from BDH Laboratory Chemicals, optionally together with a thickener such as PVP, as part of the aqueous-based compositions to be used for printing patchwise releasable reagent layers and hydrophilic (e.g., cellulose acetate) membrane layers.

The several features and characteristics described herein, including those referred to in the claims and illustrated in and by the drawings, are disclosed and can be used in all combinations, subcombinations and variations, as may be desired.

We claim:

1. A potentiometric electrochemical analysis method, which comprises placing by capillary action an aqueous sample liquid to be tested for the presence of a quantity of an analyte in said sample liquid, in each of two compartments of an electrochemical analysis cell, wherein the aqueous sample liquid so placed in each compartment is in electrochemical contact with one of two electrodes forming part of the cell, wherein the electrodes are insensitive to the analyte, and wherein the compartments are separated by an electroactive barrier which is sensitive to or selective for the analyte, said barrier not being in electrical contact with either electrode except through the medium of the sample liquid, said method further comprising changing the amount of the analyte material in a selected one of the compartments by adding thereto a predefined standard quantity of analyte, measuring the resulting cell potential and determining therefrom the concentration of analyte in the sample liquid being tested, the predefined standard quantity of analyte being allowed to dissolve in said sample liquid from a dry material being free from any electroactive material to which the electrodes are sensitive.

2. A method according to claim 1, wherein said analyte comprises potassium, sodium or ammonium ions, said electrodes are halide-sensitive electrodes, said dry material is a halide-free salt of the analyte ion, and said electroactive barrier is plasticised pvc membrane containing an effective quantity of a corresponding ionophore to confer electrochemical sensitivity or selectivity for said ion thereon.

* * * * *